United States Patent
Jung et al.

(10) Patent No.: US 8,217,366 B2
(45) Date of Patent: Jul. 10, 2012

(54) CARBON ION GENERATING DEVICE AND TUMOR TREATMENT APPARATUS USING THE SAME

(75) Inventors: Moon-Youn Jung, Daejeon (KR); Nam Soo Myung, Seongnam (KR); Hyun Woo Song, Daejeon (KR); Hyeon-Bong Pyo, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 181 days.

(21) Appl. No.: 12/846,525

(22) Filed: Jul. 29, 2010

(65) Prior Publication Data
US 2011/0101237 A1    May 5, 2011

(30) Foreign Application Priority Data

Nov. 2, 2009 (KR) .......................... 10-2009-0105089
Mar. 24, 2010 (KR) .......................... 10-2010-0026419

(51) Int. Cl.
*H01J 27/02* (2006.01)
*H01J 49/10* (2006.01)
*A61N 5/00* (2006.01)

(52) U.S. Cl. ............. 250/423 R; 250/423 F; 250/492.3; 313/310; 313/311; 977/949; 423/445 R

(58) Field of Classification Search ............ 250/423 R, 250/423 F, 492.3; 977/949; 313/310, 311; 423/445 R See application file for complete search history.

(56) References Cited

U.S. PATENT DOCUMENTS

| 6,664,728 | B2 * | 12/2003 | Pavlovsky et al. ............ 313/495 |
| 6,787,122 | B2 * | 9/2004 | Zhou ........................ 423/447.1 |
| 7,129,513 | B2 * | 10/2006 | Zhou et al. ...................... 257/10 |
| 2003/0183774 | A1 | 10/2003 | Tajima |
| 2008/0290299 | A1 | 11/2008 | Hansmann et al. |

FOREIGN PATENT DOCUMENTS

| DE | 10 2007 020 599 A1 | 11/2008 |
| JP | 3246364 B2 | 6/1998 |
| JP | 2009-158152 | 7/2009 |

OTHER PUBLICATIONS

Koichi Hata et al., "Field-Evaporation of Magic Cluster Ions, $C_{20}^+$, From Carbon Nanotubes", Scripta mater, 2001, pp. 1571-1574, vol. 44.

A.G. Umnov et al., "Field-induced evaporation of carbon nanotubes", Appl. Phys., 2001, pp. 301-304, A 73.

Kenneth A. Dean, et al., "Evaporation of carbon nanotubes during electron field emission", Applied Physics Letters, 2001, pp. 1873-1875, vol. 79, No. 12.

* cited by examiner

*Primary Examiner* — Nikita Wells

(57) ABSTRACT

Provided are a carbon ion generating device and a tumor treatment apparatus using the same. The carbon ion generating device includes a carbon nanostructure, a carbon emitting structure, an ionizing structure, and an accelerator. The carbon emitting structure is configured to induce an emission of carbon atoms from one end of the carbon nanostructure. The ionizing structure is configured to ionize the emitted carbon atoms. The accelerator is configured to accelerate the ionized carbon atoms.

15 Claims, 5 Drawing Sheets

CARBON ION GENERATING DEVICE AND TUMOR TREATMENT APPARATUS USING THE SAME

CROSS-REFERENCE TO RELATED APPLICATIONS

This U.S. non-provisional patent application claims priority under 35 U.S.C. §119 of Korean Patent Application Nos. 10-2009-0105089, filed on Nov. 2, 2009, and 10-2010-0026419, filed on Mar. 24, 2010, the entire contents of which are hereby incorporated by reference.

BACKGROUND OF THE INVENTION

The present invention disclosed herein relates to tumor treatment apparatuses, and more particularly, to a carbon ion generating device and a tumor treatment apparatus using the same.

Examples of the radiation therapies include an X-ray therapy, an electron-beam therapy, and an ion-beam therapy. Among the radiation therapies, the X-ray therapy is in the most widespread use because it can be implemented at the lowest cost using the simplest device. It was discovered in 1950's that a tumor can be treated by accelerating and injecting electrons into the tumor by means of an accelerator. However, the electron-beam therapy was formally used as one of the radiation therapies in 1980's due to the implementation of miniaturized ion accelerators. The X-ray or electron-beam therapy broke hydrogen bonds in cancer cells to destroy the DNA of a cancer, but it involved the adverse effect of severely damaging healthy cells on the propagation path. In order to reduce the damage to healthy cells, the technologies of Intensity-Modulated Radiation Therapy (IMRT), Tomotherapy and Cyber Knife have been developed, but they have failed to completely prevent the above adverse effect.

The ion-beam therapy is esteemed as a treatment method that can reduce the adverse effect in the X-ray or electron-beam therapy. Like electrons, an ion beam must be accelerated to a high velocity in order to penetrate a material. The velocity of an ion beam decreases gradually while the ion beam penetrates a material. However, the ion beam undergoes the most energy loss of ionizing radiation immediately before stopping, which is called Bragg peak, for William Henry Bragg who discovered it in 1903. Thus, when the velocity of ions is accurately controlled, the ion-beam therapy can provide a selective local treatment for malignant tumors.

In view of acceleration energy, hydrogen ions (i.e., protons), which are the lightest among all the ions, have been considered as a material for the ion-beam therapy. However, a carbon-ion therapy has recently been esteemed since it was discovered that carbon ions have better biological effects than protons. For example, it was reported that carbon ions are 2.8 times higher in cancer cell kill rate than protons and are 2.5 times lower in cancer recurrence rate than X-rays or protons.

SUMMARY OF THE INVENTION

The present invention provides a carbon ion generating device for generating high-purity carbon ions.

The present invention also provides a tumor treatment apparatus using high-purity carbon ions.

In some embodiments of the present invention, carbon ion generating devices include: a carbon nanostructure; a carbon emitting structure configured to induce an emission of carbon atoms from one end of the carbon nanostructure; and an ionizing structure configured to ionize the emitted carbon atoms.

In some embodiments, the carbon emitting structure includes an electron emission inducing unit configured to induce an electron emission from the one end of the carbon nanostructure. Herein, the electron emission may heat the one end of the carbon nanostructure to induce the emission of the carbon atoms. The electron emission inducing unit may include an electric field creating unit configured to create an electric field with an intensity for induction of an electron emission in a space where the carbon nanostructure is located. For example, the electric field creating unit includes: a top electrode disposed adjacent to the one end of the carbon nanostructure; a bottom electrode connected to the other end of the carbon nanostructure; and a power supply unit configured to create a first potential difference between the top electrode and the bottom electrode. Herein, the first potential difference may be greater than a minimum voltage for induction of the electron emission from the one end of the carbon nanostructure.

In other embodiments, the carbon emitting structure further includes an ion beam emitting unit configured to perform an ion bombardment to the one end of the carbon nanostructure. For example, the ion beam emitting unit is configured to bombard argon ions to the one end of the carbon nanostructure.

In further embodiments, the ionizing structure includes a charged particle emitting unit configured to create charged particles that electrically interact with the emitted carbon atoms to ionize the emitted carbon atoms. Herein, the charged particles may be electrons having a kinetic energy greater than the ionization energy of carbon atoms.

In further embodiments, the carbon nanostructure includes at least one of a single-walled nanotube, a multi-walled carbon nanotube, a dual-walled carbon nanotube, a carbon nanohorn, and a nanotube rope. Also, the carbon nanostructure may include a carbon nanotube formed using one of electrical discharge, laser deposition, thermal chemical vapor deposition, and plasma chemical vapor deposition.

In other embodiments of the present invention, tumor treatment apparatuses include: a carbon nanostructure; a carbon emitting structure configured to induce an emission of carbon atoms from one end of the carbon nanostructure; an ionizing structure configured to ionize the emitted carbon atoms; and an accelerator configured to accelerate the ionized carbon atoms.

In some embodiments, the accelerator includes at least one of a linear accelerator, a cyclotron, a synchrocyclotron, and a synchrotron. The tumor treatment apparatuses may further include a control unit configured to control the acceleration process of the ionized carbon atoms in the accelerator.

In other embodiments, the carbon nanostructure includes carbon nanotubes formed using chemical vapor deposition. The tumor treatment apparatuses may further include a guide unit configured to inject the ionized carbon atoms into the accelerator.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Exemplary embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

Figure 1:
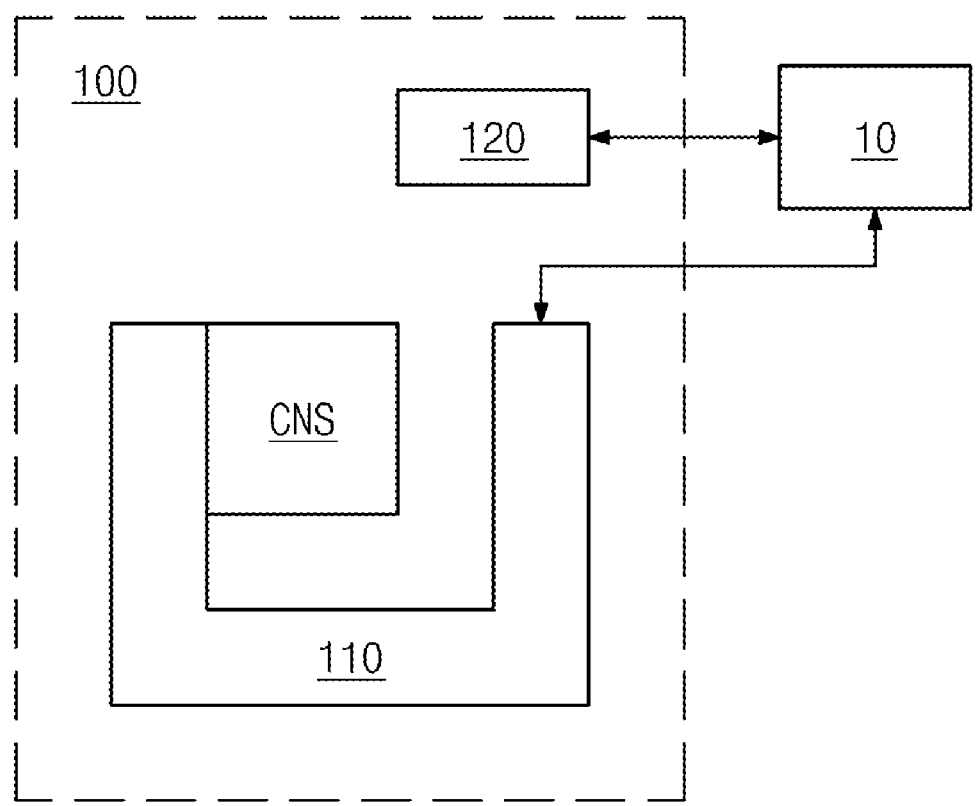
FIG. 1 is a schematic block diagram of a carbon ion generating device according to an exemplary embodiment of the present invention.

FIG. 1 is a schematic block diagram of a carbon ion generating device according to an exemplary embodiment of the present invention.

Referring to FIG. 1, a carbon ion generating device 100 may include a carbon nanostructure CNS, a carbon emitting structure 110 configured to induce an emission of carbon atoms from one end of the carbon nanostructure CNS, and an ionizing structure 120 configured to ionize the emitted carbon atoms.

The carbon nanostructure CNS may include at least one of a single-walled nanotube, a multi-walled carbon nanotube, a dual-walled carbon nanotube, a carbon nanohorn, and a nanotube rope. Also, the carbon nanostructure CNS may be formed using one of various processes. For example, the carbon nanostructure CNS may include a carbon nanotube formed using one of electrical discharge, laser deposition, thermal chemical vapor deposition, and plasma chemical vapor deposition.

If the crystalline structure of the carbon nanotube or the carbon nanostructure CNS has high completeness (or crystallinity), the emission of carbon atoms by the carbon emitting structure 110 may be difficult or the energy consumption of the carbon emitting structure 110 for the emission of carbon atoms may be excessive. Therefore, according to an exemplary embodiment of the present invention, the carbon nanostructure CNS may be formed through a fabrication process capable of relatively degrading the crystallinity of the carbon nanostructure CNS. For example, the carbon nanostructure CNS may be formed using one of chemical vapor deposition processes. The reason for this is that carbon nanotubes grown through chemical vapor deposition processes may have lower crystallinity than carbon nanotubes grown through an electrical discharge process and a laser deposition process, because the chemical vapor deposition processes are performed under lower temperature conditions than the electrical discharge process and the laser deposition process.

According to an exemplary embodiment of the present invention, the carbon emitting structure 110 may be configured to emit carbon atoms from the one end of the carbon nanostructure CNS by using Joule's heat generated by an electron emission phenomenon at the one end of the carbon nanostructure CNS. As is well known in the art, an electric field concentrates at a protruding portion of a conductor. Therefore, electrons can be easily emitted from the protruding portion. Also, the electron emission heats the protruding portion to a high temperature to induce an emission of its atoms. Likewise, the concentration of an electric field and the resulting Joule's heat may induce an emission of carbon atoms from a carbon nanotube. In this embodiment, the carbon emitting structure 110 may be configured to use such a carbon atom emission phenomenon. The configuration and operation of the carbon emitting structure 110 will be described later in detail with reference to FIGS. 2 to 4.

The well-known field emission display (FED) is an example of the display technology using the field emission phenomenon. In the FED technology field, a carbon atom emission phenomenon resulting from Joule's heat causes a technical problem of a loss of an electrode (i.e., a carbon nanotube). However, according to this embodiment, such a technical problem (i.e., a carbon atom emission phenomenon resulting from Joule's heat) may be intentionally used to obtain carbon atoms separated from the carbon nanotube.

According to an exemplary embodiment of the present invention, the carbon emitting structure 110 may be configured to use an ion bombardment to emit carbon atoms from the one end of the carbon nanostructure CNS. If ions are injected with a predetermined kinetic energy into the one end of the carbon nanostructure CNS, carbon ions may be separated from the carbon nanostructure CNS as a result of the mechanical interaction between the injected ions and the carbon atoms of the carbon nanostructure CNS.

According to a modified embodiment of the present invention, the carbon atom emission resulting from the ion bombardment may be used to facilitate the carbon atom emission resulting from the electric field concentration, which will be described later in detail with reference to FIGS. 3 and 4. Likewise, the carbon atom emission resulting from the electric field concentration may be used to facilitate the carbon atom emission resulting from the ion bombardment.

The ionizing structure 120 may be configured to ionize the carbon atoms emitted by the carbon emitting structure 110. The ionization of neutral atoms may be implemented by various methods, and the ionizing structure 120 may be configured using one of such various methods. The configuration and operation of the ionizing structure 120 will be described later in detail with reference to FIGS. 2 to 4.

A control unit 10 may be configured to monitor/control the operation of the carbon emitting structure 110 and the operation of the ionizing structure 120 and to display information related to the control operations to a user. To this end, the control unit 10 may include a user interface and a unit for electronic communication with the carbon emitting structure 110, the ionizing structure 120 and power supplies thereof.

Figure 2:
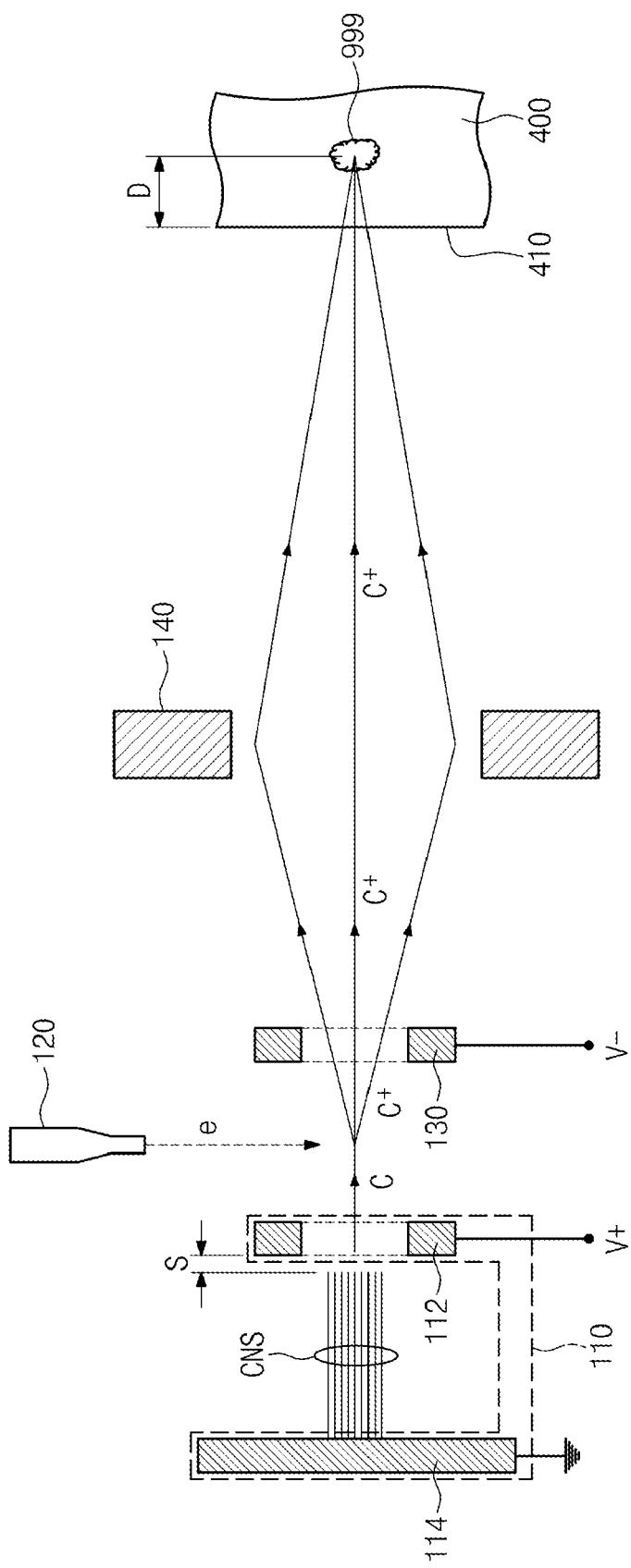
FIGS. 2 to 4 are diagrams illustrating examples of a tumor treatment apparatus using the carbon ion generating device described with reference to FIG. 1.
Figure 3:
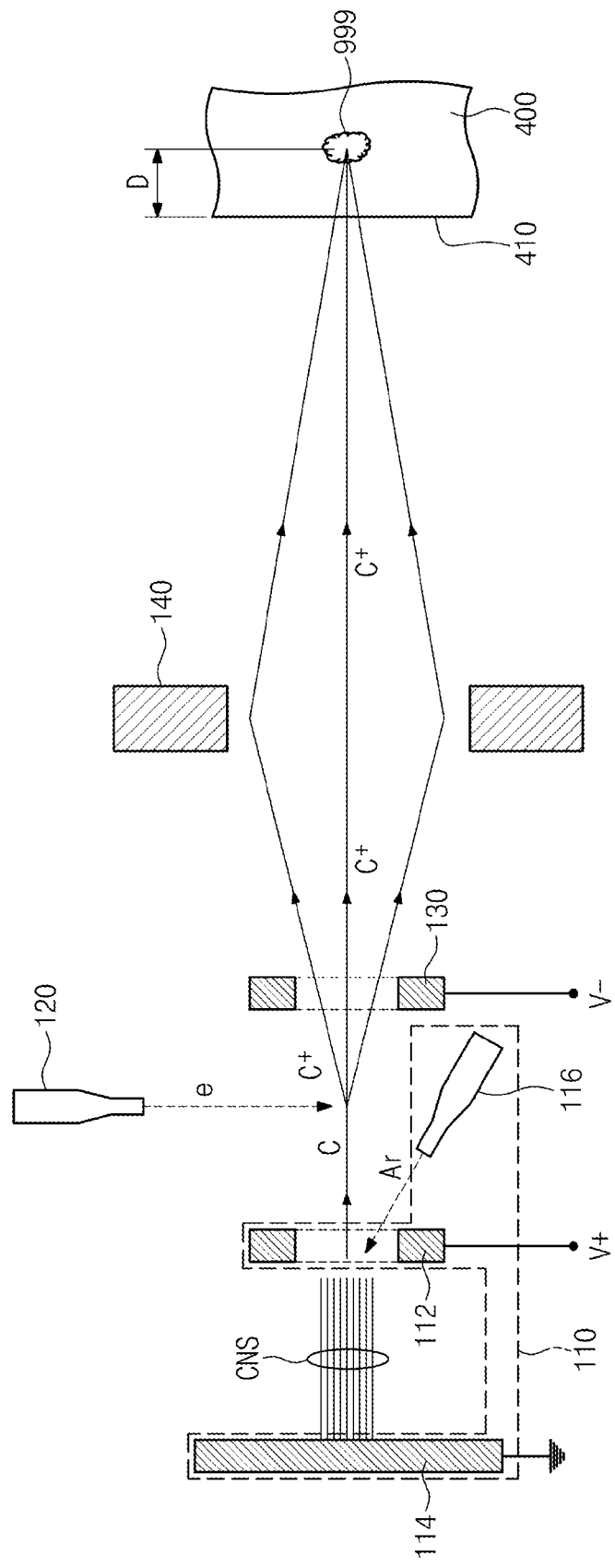
Figure 4:
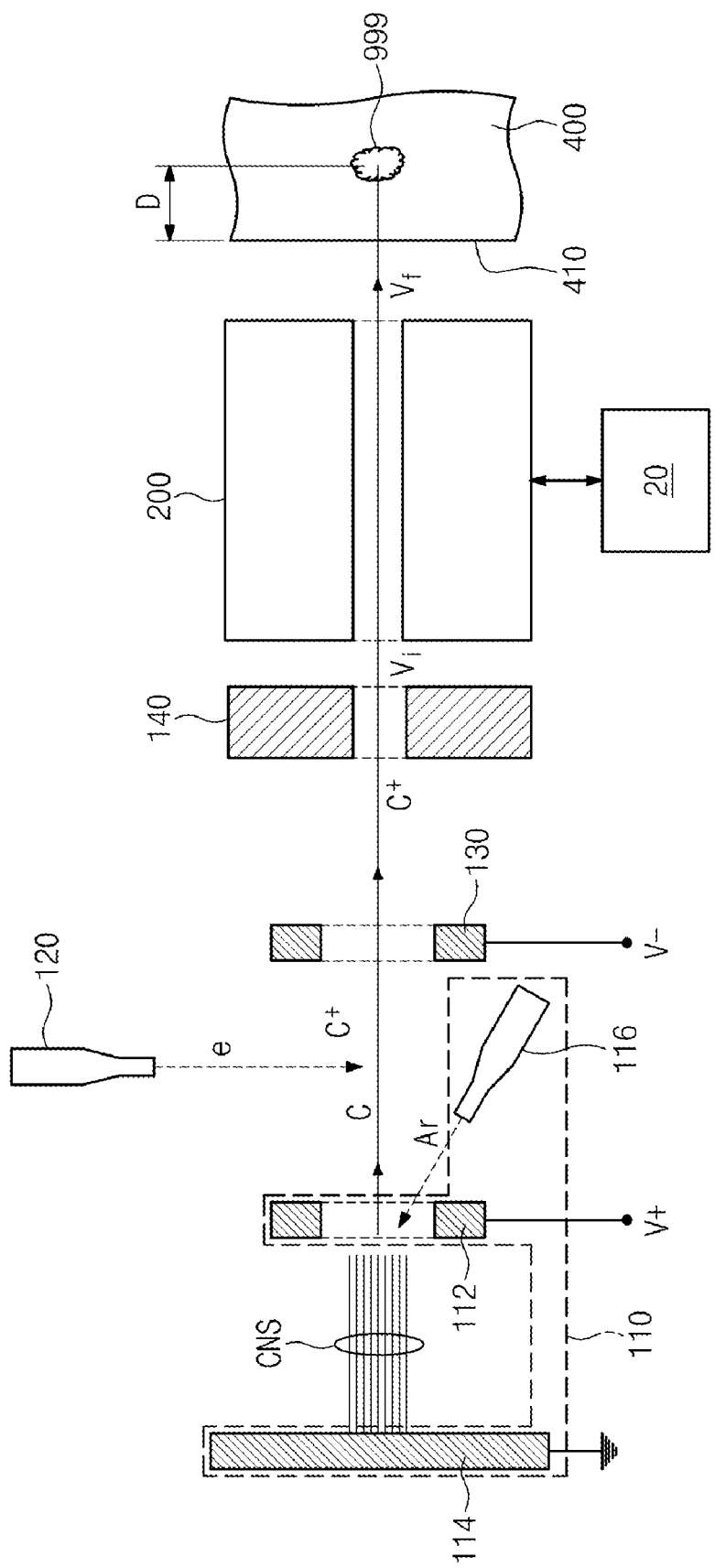

FIGS. 2 to 4 are diagrams illustrating examples of a tumor treatment apparatus using the carbon ion generating device described with reference to FIG. 1. A description of technical features overlapping with the embodiment of FIG. 1 will be omitted for conciseness.

Referring to FIGS. 2 to 4, the carbon emitting structure 110 may include a top electrode 112 disposed adjacent to the one end of the carbon nanostructure CNS, and a bottom electrode 114 connected to the other end of the carbon nanostructure CNS. A space S between the top electrode 112 and the one end of the carbon nanostructure CNS and a difference between voltages applied thereto may be configured to induce an electron emission from the one end of the carbon nanostructure CNS. According to an exemplary embodiment, a ground voltage GND is applied to the bottom electrode 114 and a first positive voltage V+ is applied to the top electrode 112. The space S and the potential difference V+ may be designed to create an electric field of at least $10^8$ V/m at the one end of the carbon nanostructure CNS.

As illustrated in FIGS. 3 and 4, the carbon emitting structure 110 may further include an ion beam emitting unit 116. The ion beam emitting unit 116 may be configured to implement the ion bombardment and the resulting carbon atom emission. According to an exemplary embodiment, the ion beam emitting unit 116 is configured to bombard argon ions to the one end of the carbon nanostructure CNS.

Figure 5:
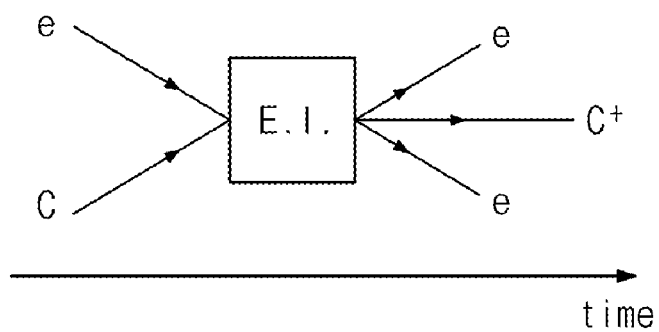
FIG. 5 is a diagram illustrating an aspect of the embodiments based on the technical concept of the present invention.

The ionizing structure 120 may be an electron beam emitting unit configured to irradiate an electron beam onto the emitted carbon atoms. As illustrated in FIG. 5, the electrons emitted from the electron beam emitting unit may participate in an electrical interaction that causes the outermost electrons of the emitted carbon atoms to become free electrons. To this end, the electrons constituting the electron beam may be prepared to have a kinetic energy greater than the ionization energy of the carbon atoms. According to an exemplary embodiment, the ionizing structure 120 may include a filament for electron emission.

As described above, when the carbon ions have positive charge and a positive voltage is applied to the top electrode 112, a repulsive force acts between the top electrode 112 and the carbon ions. That is, a force directed away from the top electrode 112 is applied to the carbon ions. However, the repulsive force by the top electrode 112 may be insufficient to accelerate the carbon ions to a velocity sufficient for medical purposes.

In order to overcome this problem, a tumor treatment apparatus according to the present invention may further include units configured to accelerate the ionized carbon atoms toward a predetermined target point (i.e., a tumor 999). For example, as illustrated in FIGS. 2 to 4, a first acceleration electrode 130 may be disposed between the ionizing structure 120 and the target point 999 to primarily accelerate the carbon ions. A second voltage V− may be applied to the first acceleration electrode 130, and the polarity of the second voltage V− may be selected to apply an attractive force between the first acceleration electrode 130 and the carbon ions. For example, when the carbon ions have positive charge, a negative voltage may be applied to the first acceleration electrode 130. In this case, since a force directed toward the first acceleration electrode 130 is applied to the carbon ions, the carbon ions may be accelerated toward the target point 999 by the resultant force of the repulsive force by the top electrode 112 and the attractive force by the first acceleration electrode 130.

At the initial acceleration time point, the carbon ions may be accelerated in various directions. Also, the attractive force on the carbon ions by the first acceleration electrode 130 may induce a deflection of the path of the carbon ions, and the deflection may cause the carbon ions to recede from the first acceleration electrode 130, thus increasing the distance therebetween. In order to overcome this problem, the tumor treatment apparatus may further include a guide structure 140 configured to guide/concentrate the accelerated carbon ions to the target point 999 by the electromagnetic effects, as illustrated in FIGS. 2 and 4. Also, the guide structure 140 may be configured to accelerate the accelerated carbon ions to a higher velocity by the electromagnetic effects. The electromagnetic effects used to guide/concentrate/accelerate the carbon ions may include various effects that can be described by the electromagnetic force that can be expressed as the resultant force of Coulomb force and Lorentz force.

The location of a Bragg peak is determined by the injection velocity at which the carbon ions are injected into the surface 410 of an organism (e.g., the skin of a human). Thus, when the distance L between the target point 999 and the surface 410 is large, the injection velocity of the carbon ions must be sufficiently high. According to some embodiments of the present invention, as illustrated in FIG. 4, the tumor treatment apparatus may further include an accelerator 200 configured to accelerate the carbon ions to a desired injection velocity, in addition to the guide structure 140 or the first acceleration electrode 130 configured to primarily accelerate the carbon ions. That is, the accelerator 200 may be configured to use the known physical effect to cause the final velocity $v_f$ of the carbon ions emitted therefrom to be higher than the initial velocity $v_i$ of the carbon ions injected thereinto. According to some embodiments, the accelerator 200 may include at least one of a linear accelerator, an electrostatic accelerator, a cyclotron, a synchrocyclotron, and a synchrotron, each of which may be configured to have one of the accelerator structures based on the technologies known in the field of particle collider physics, or a modified structure thereof. The acceleration of the carbon ions by the accelerator 200 may be performed in consideration of the electromagnetic effects and the special relativistic effects, and the tumor treatment apparatus may further include an accelerator control unit 20 configured to control the acceleration process. The accelerator control unit 20 may be configured to cooperate with the control unit 10 of the carbon ion generating device 100 described with reference to FIG. 1. To this end, the accelerator control unit 20 and the control unit 10 may be configured to communicate with each other electronically.

Figure 6:
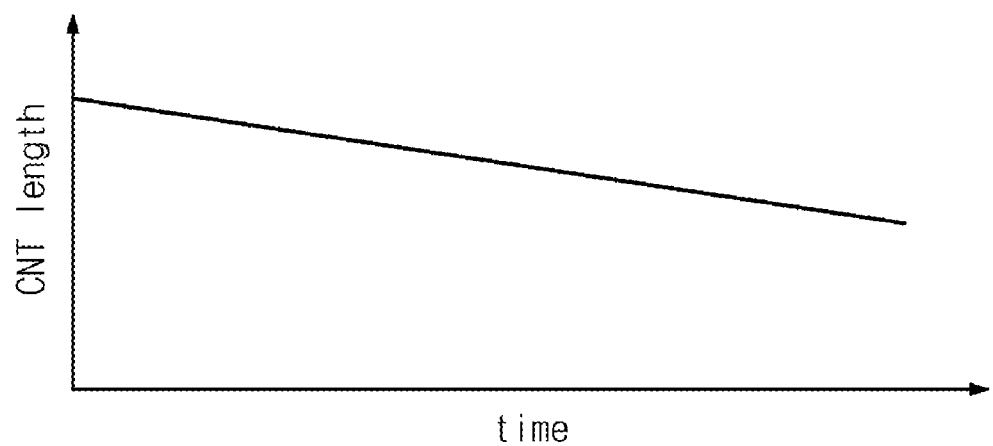
FIG. 6 is a graph illustrating another aspect of the embodiments based on the technical concept of the present invention.

FIG. 6 is a graph illustrating an aspect of the present invention. According to the embodiments based on the technical concept of the present invention, the carbon nanostructure CNS is used as a source material for generating the carbon ions. Accordingly, as illustrated in FIG. 6, the length of the carbon nanostructure CNS (e.g., the carbon nanotube) represented by the vertical axis may decrease gradually with an increase in the use time of the carbon ion generating device 100 represented by the horizontal axis. According to embodiments of the present invention, the carbon ion generating device 100 intentionally uses such a technical aspect that is a technical problem in the field effect display (FED) technology.

As described above, the present invention provides a carbon ion generating device for generating carbon ions from a carbon nanotube, and a tumor treatment apparatus using the same. Carbon ions generated according to the present invention can have high purity because they are generated from a carbon nanotube. Accordingly, it is possible to prevent impurities (other than carbon ions) from being used in a tumor treatment process.

The above-disclosed subject matter is to be considered illustrative and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A carbon ion generating device comprising:
   a carbon nanostructure;
   a carbon emitting structure configured to induce an emission of carbon atoms from one end of the carbon nanostructure; and
   an ionizing structure configured to ionize the emitted carbon atoms; a top electrode disposed adjacent to the one end of the carbon nanostructure;

a bottom electrode connected to the other end of the carbon nanostructure; and a power supply unit configured to create a first potential difference between the top electrode and the bottom electrode.

2. The carbon ion generating device of claim 1, wherein the carbon emitting structure comprises an electron emission inducing unit configured to induce an electron emission from the one end of the carbon nanostructure, wherein the electron emission heats the one end of the carbon nanostructure to induce the emission of the carbon atoms.

3. The carbon ion generating device of claim 2, wherein the electron emission inducing unit comprises an electric field creating unit configured to create an electric field with an intensity for induction of an electron emission in a space where the carbon nanostructure is located.

4. The carbon ion generating device of claim 3,
wherein the first potential difference is greater than a minimum voltage for induction of the electron emission from the one end of the carbon nanostructure.

5. The carbon ion generating device of claim 2, wherein the carbon emitting structure further comprises an ion beam emitting unit configured to bombard the one end of the carbon nanostructure with ions.

6. The carbon ion generating device of claim 5, wherein the ion beam emitting unit is configured to bombard the one end of the carbon nanostructure with argon ions.

7. The carbon ion generating device of claim 1, wherein the ionizing structure comprises a charged particle emitting unit configured to generate charged particles, the charged particles interacting electrically with the emitted carbon atoms and thereby ionizing the emitted carbon atoms.

8. The carbon ion generating device of claim 7, wherein the charged particles are electrons having a kinetic energy greater than the ionization energy of carbon atoms.

9. The carbon ion generating device of claim 1, wherein the carbon nanostructure comprises at least one of a single-walled nanotube, a multi-walled carbon nanotube, a dual-walled carbon nanotube, a carbon nanohorn, and a nanotube rope.

10. The carbon ion generating device of claim 1, wherein the carbon nanostructure comprises a carbon nanotube formed using one of electrical discharge, laser deposition, thermal chemical vapor deposition, and plasma chemical vapor deposition.

11. A tumor treatment apparatus comprising:
a carbon nanostructure;
a carbon emitting structure configured to induce an emission of carbon atoms from one end of the carbon nanostructure;
an ionizing structure configured to ionize the emitted carbon atoms;
a top electrode disposed adjacent to the one end of the carbon nanostructure;
a bottom electrode connected to the other end of the carbon nanostructure;
a power supply unit configured to create a first potential difference between the top electrode and the bottom electrode; and
an accelerator configured to accelerate the ionized carbon atoms.

12. The tumor treatment apparatus of claim 11, wherein the accelerator comprises at least one of a linear accelerator, a cyclotron, a synchrocyclotron, and a synchrotron.

13. The tumor treatment apparatus of claim 11, further comprising a control unit configured to control the acceleration process of the ionized carbon atoms in the accelerator.

14. The tumor treatment apparatus of claim 11, wherein the carbon nanostructure comprises carbon nanotubes formed using chemical vapor deposition.

15. The tumor treatment apparatus of claim 11, further comprising a guide unit configured to inject the ionized carbon atoms into the accelerator.

* * * * *